(12) United States Patent
Tanishima et al.

(10) Patent No.: US 9,827,175 B2
(45) Date of Patent: Nov. 28, 2017

(54) OIL-IN-WATER EMULSIFIED SKIN COSMETIC COMPOSITION

(71) Applicant: KAO CORPORATION, Chuo-ku (JP)

(72) Inventors: Takashi Tanishima, Chiyoda-ku (JP); Aki Yuyama, Soka (JP); Shinichi Tsukii, Koshigaya (JP)

(73) Assignee: KAO CORPORATION, Chuo-ku (JP)

( * ) Notice: Subject to any disclaimer, the term of this patent is extended or adjusted under 35 U.S.C. 154(b) by 456 days.

(21) Appl. No.: 14/298,022

(22) Filed: Jun. 6, 2014

(65) Prior Publication Data

US 2014/0363475 A1 Dec. 11, 2014

(30) Foreign Application Priority Data

Jun. 7, 2013 (JP) ................. 2013-120764

(51) Int. Cl.
*A61K 8/02* (2006.01)
*A61K 8/06* (2006.01)
*A61K 8/41* (2006.01)
*A61K 8/42* (2006.01)
*A61Q 19/00* (2006.01)
*A61K 8/31* (2006.01)
*A61K 8/37* (2006.01)
*A61K 8/86* (2006.01)
*A61K 8/92* (2006.01)
*A61Q 1/02* (2006.01)

(52) U.S. Cl.
CPC ............... *A61K 8/062* (2013.01); *A61K 8/31* (2013.01); *A61K 8/37* (2013.01); *A61K 8/416* (2013.01); *A61K 8/42* (2013.01); *A61K 8/86* (2013.01); *A61K 8/92* (2013.01); *A61K 8/922* (2013.01); *A61Q 19/00* (2013.01); *A61K 2800/10* (2013.01); *A61Q 1/02* (2013.01)

(58) Field of Classification Search
CPC . A61K 8/97; A61K 8/365; A61K 8/64; A61K 8/8158; A61K 8/8182; A61K 8/062; A61K 8/60; A61K 8/63; A61Q 13/00; A61Q 19/007; A61Q 1/14; A61Q 7/00; A61Q 19/001; A61Q 19/002; A61Q 19/008; A61Q 1/10; A61Q 1/12; A61Q 5/04

See application file for complete search history.

(56) References Cited

U.S. PATENT DOCUMENTS

| | | | |
|---|---|---|---|
| 2001/0047039 A1 | 11/2001 | McManus et al. | |
| 2002/0058052 A1* | 5/2002 | Hasebe | A61K 8/39 424/401 |
| 2007/0293577 A1 | 12/2007 | Kamachi et al. | |
| 2010/0080764 A1* | 4/2010 | Fox | A61K 8/64 424/60 |
| 2012/0172433 A1 | 7/2012 | Yamamoto et al. | |
| 2012/0189675 A1 | 7/2012 | Matsuo et al. | |

FOREIGN PATENT DOCUMENTS

| | | | |
|---|---|---|---|
| CN | 1258492 A | | 7/2000 |
| JP | 6-9329 | | 1/1994 |
| JP | 7-206629 | | 8/1995 |
| JP | 2002114631 | * | 4/2002 |
| JP | 2002114631 A | * | 4/2002 |
| JP | 2002-348214 | | 12/2002 |
| JP | 2006-56852 | | 3/2006 |
| JP | 2010-254677 | | 11/2010 |
| JP | 2010-270078 | | 12/2010 |
| JP | 2012-140340 | | 7/2012 |
| JP | 2012-250916 | | 12/2012 |
| JP | 2013-537166 | | 9/2013 |
| JP | 2013-199442 | | 10/2013 |
| JP | 2014-108926 A | | 6/2014 |
| WO | WO 95/05153 | | 2/1995 |

* cited by examiner

*Primary Examiner* — Nannette Holloman
(74) *Attorney, Agent, or Firm* — Oblon, McClelland, Maier & Neustadt, L.L.P.

(57) ABSTRACT

An oil-in-water emulsion skin cosmetic composition comprising the following components (A), (B), (C), (D) and (E):
(A) from 1 to 10% by mass of an oil agent which is liquid at 25° C.,
(B) from 1 to 6% by mass of an oil agent which is solid or semi-solid at 25° C.,
(C) from 0.7 to 3.5% by mass of linear alcohol having 12 to 22 carbon atoms,
(D) from 0.2 to 1% by mass of at least one selected from the group consisting of an ionic surfactant and a nonionic surfactant having an HLB of 12.5 to 15, and
(E) water, wherein
the mass ratio of the component (B) to the component (A), (B)/(A), is from 0.3 to 1.0, and
emulsion particles have a number-average particle diameter of 1.0 to 3.0 μm.

10 Claims, No Drawings

OIL-IN-WATER EMULSIFIED SKIN COSMETIC COMPOSITION

FIELD OF THE INVENTION

The present invention relates to an oil-in-water emulsion skin cosmetic composition.

BACKGROUND OF THE INVENTION

Women use cosmetic compositions for demonstrating their beautiful skin. Such beautiful skin required by women is highly uniform skin, and specifically, it is skin having neither color unevenness nor asperity. In order to diminish such color unevenness on the skin, it is important to impart covering power to cosmetics. However, in recent years, natural feeling has tended to be preferable. Thus, it has been desired to naturally cover skin color unevenness or asperity. For example, with regard to cosmetic compositions which produce a transparent finishing without unnatural concealing power and also cover skin color unevenness or asperity, the following cosmetic compositions have been studied: a powdery cosmetic composition comprising metal oxide powders such as titanium oxide and zinc oxide and spherical elastic resin powders (Patent Document 1), and a water-in-oil emulsion cosmetic composition comprising volatile oil, non-volatile oil and silicone elastic powders, which provides good usability and produces a natural skin finishing, while covering skin color unevenness such as spots and freckles, skin asperity such as pores and wrinkles (Patent Document 2), and the like.

Moreover, with regard to cosmetic compositions capable of concealing pores by imparting to the skin, suitable translucency, makeup effect, and the water-proofness and sebum-proofness of the film, without concerns about heavy makeup and makeup deterioration, the following cosmetic composition has been studied: a cosmetic composition characterized in that it comprises a solid component, powders consisting of a white pigment and/or an extender pigment, and a non-volatile oil material (Patent Document 3), and with regard to an oil-in-water emulsion cosmetic composition capable of providing excellent feeling of tension to the skin without providing stickiness and capable of providing excellent preservation stability, the following cosmetic composition has been studied: a cosmetic composition comprising lecithin, a nonionic surfactant, liquid oil which is liquid at ordinary temperature, solid oil which is solid at ordinary temperature, polyhydric alcohol, and water, wherein the liquid oil comprises at least one cyclic silicone, and wherein the solid oil comprises shea butter (Patent Document 4).

(Patent Document 1) JP-A-2012-140340
(Patent Document 2) JP-A-2006-56852
(Patent Document 3) JP-A-6-9329
(Patent Document 4) JP-A-2012-250916

SUMMARY OF THE INVENTION

The present invention relates to an oil-in-water emulsion skin cosmetic composition comprising the following components (A), (B), (C), (D) and (E):
(A) from 1 to 10% by mass of an oil agent which is liquid at 25° C.,
(B) from 1 to 6% by mass of an oil agent which is solid or semi-solid at 25° C.,
(C) from 0.7 to 3.5% by mass of linear alcohol having 12 to 22 carbon atoms,
(D) from 0.2 to 1% by mass of at least one selected from the group consisting of an ionic surfactant and a nonionic surfactant having an HLB of 12.5 to 15, and
(E) water, wherein
the mass ratio of the component (B) to the component (A), (B)/(A), is from 0.3 to 1.0, and
emulsion particles have a number-average particle diameter of 1.0 to 3.0 μm.

DETAILED DESCRIPTION OF THE INVENTION

White pigments such as titanium oxide and zinc oxide are problematic in that these substances would cause color migration to clothes when they are used. When powders are used, they would cause a feeling of strangeness if they are too light, and as a result, such powders are problematic in that it is difficult to apply additional applications of the powders. Hence, it has been desired to develop a cosmetic composition having functions of providing a natural feel to the touch and diminishing skin color unevenness, without color migration to clothes and the like.

The present inventors found that an oil-in-water emulsion skin cosmetic composition, which overcomes the aforementioned problems, can be obtained by using two specific oil agents, higher alcohol, and a surfactant at a specific ratio.

The oil-in-water emulsion skin cosmetic composition of the present invention is able to diminish color unevenness on the skin and naturally cover the skin. In addition, the present oil-in-water emulsion skin cosmetic composition has excellent usability and high preservation stability, without having stickiness.

The oil agent as component (A) is liquid at 25° C. The term "liquid" is used herein to mean that the viscosity at 25° C. is 10,000 mPa·s or less. The viscosity can be measured using a type B viscometer (VISCOMETER TVB-10, manufactured by Toki Sangyo Co., Ltd.). A component with a viscosity of less than 200 mPa·s can be measured with Rotor No. 1 at 30 rpm for 1 minute; a component with a viscosity which is in a range of 200 mPa·s or more and less than 4,000 mPa·s can be measured with Rotor No. 3 at 30 rpm for 1 minute; and a component with a viscosity which is in a range of 4,000 mPa·s or more and 10,000 mPa·s or less can be measured with Rotor No. 3 at 6 rpm for 1 minute.

The type of such a liquid oil agent is not limited, as long as it is generally used for cosmetic compositions. Examples of the liquid oil agent include linear or branched hydrocarbon oils, such as liquid paraffin, light isoparaffin, liquid isoparaffin, squalane, and squalene; ester oils including vegetable oils such as jojoba oil and olive oil, animal oils such as liquid lanolin, monoalcohol fatty acid ester, and polyhydric alcohol fatty acid ester; silicone oils, such as dimethyl polysiloxane, dimethyl cyclopolysiloxane, methyl phenyl polysiloxane, methyl hydrogen polysiloxane, and higher alcohol-modified organopolysiloxane; and fluorine oils such as fluoropolyether, perfluoroalkylether silicone. Among these substances, hydrocarbon oil, ester oil, and silicone oil are preferable in terms of usability such as smoothness upon application. Hydrocarbon oil and ester oil are more preferable, and ester oil is even more preferable.

As hydrocarbon oil, from the viewpoints of usability such as smoothness upon application and prevention of stickiness, hydrocarbon oil having a viscosity at 25° C. of 100 mPa·s or less is preferable, hydrocarbon oil having a viscosity at 25° C. of 60 mPa·s or less is more preferable, hydrocarbon oil having a viscosity at 25° C. of 35 mPa·s or less is even more preferable, and hydrocarbon oil having a viscosity at 25° C. of 1 mPa·s or more is preferable, hydrocarbon oil having a viscosity at 25° C. of 5 mPa·s or more is more preferable, and hydrocarbon oil having a viscosity at 25° C. of 10 mPa·s or more is even more preferable. Light isoparaffin, liquid isoparaffin and squalane are preferable, and liquid isoparaffin and squalane are more preferable.

With regard to hydrocarbon, commercially available products can be used. For example, ParLeam EX (11 mPa·s) (manufactured by NOF Corporation) can be used as liquid isoparaffin, and Nikkol Squalane (30 mPa·s) (manufactured by Nikko Chemicals Co., Ltd.) can be used as squalane.

As ester oil, from the viewpoints of usability such as smoothness upon application and prevention of stickiness, ester oil having a viscosity at 25° C. of 200 mPa·s or less is preferable, ester oil having a viscosity at 25° C. of 150 mPa·s or less is more preferable, ester oil having a viscosity at 25° C. of 100 mPa·s or less is even more preferable, and ester oil having a viscosity at 25° C. of 1 mPa·s or more is preferable, ester oil having a viscosity at 25° C. of 5 mPa·s or more is more preferable, and ester oil having a viscosity at 25° C. of 10 mPa·s or more is even more preferable. Specific examples of such ester oil include isononyl isononanoate, isotridecyl isononanoate, octyl dodecyl myristate, isopropyl palmitate, isopropyl isostearate, butyl stearate, myristyl myristate, isopropyl myristate, octyl dodecyl myristate, neopentyl glycol dicaprate, tricaproin, pentaerythrityl 2-ethylhexanoate, meadowfoam oil, and olive oil. From the viewpoints of usability such as smoothness upon application and prevention of stickiness, olive oil, neopentyl glycol dicaprate, and isotridecyl isononanoate are preferable.

With regard to ester oil, commercially available products can be used. For example, Cropure OL-LQ-(JP) (90 mPa·s) (manufactured by Croda Japan K. K.) can be used as olive oil; Estemol N-01 (19 mPa·s) (manufactured by the Nisshin OiliO Group, Ltd.) can be used as neopentyl glycol dicaprate; and Salacos 913 (11 mPa·s) (manufactured by the Nisshin OiliO Group, Ltd.) can be used as isotridecyl isononanoate.

As silicone oil, from the viewpoints of usability such as smoothness upon application and prevention of stickiness, silicone oil having a viscosity at 25° C. of 50 mPa·s or less is preferable, silicone oil having a viscosity at 25° C. of 20 mPa·s or less is more preferable, silicone oil having a viscosity at 25° C. of 10 mPa·s or less is even more preferable, and silicone oil having a viscosity at 25° C. of 1 mPa·s or more is preferable, silicone oil having a viscosity at 25° C. of 2 mPa·s or more is more preferable, and silicone oil having a viscosity at 25° C. of 4 mPa·s or more is even more preferable. As such silicone oil, dimethylpolysiloxane and dimethyl cyclopolysiloxane are preferable, and dimethylpolysiloxane is more preferable.

With regard to silicone oil, commercially available products can be used. For example, KF-96A-6cs (manufactured by Shin-Etsu Chemical Co., Ltd.) can be used as dimethylpolysiloxane.

From the viewpoints of usability such as smoothness upon application and prevention of stickiness, the component (A) is preferably liquid isoparaffin, squalane, olive oil, neopentyl glycol dicaprate, isotridecyl isononanoate or dimethylpolysiloxane. It is more preferably liquid isoparaffin, squalane, olive oil, neopentyl glycol dicaprate, or isotridecyl isononanoate. It is even more preferably olive oil, neopentyl glycol dicaprate, or isotridecyl isononanoate.

As such a component (A), one or two or more components can be used in combination. From the viewpoints of usability such as smoothness upon application and prevention of stickiness, the content of the component (A) is 1% by mass or more, preferably 3% by mass or more, more preferably 5% by mass or more, and the content of the component (A) is 10% by mass or less, preferably 8% by mass or less, and more preferably 7% by mass or less, based on the entire composition. Moreover, the content of the component (A) is from 1 to 10% by mass, preferably from 3 to 8% by mass, and more preferably from 5 to 7% by mass, based on the entire composition.

The oil agent as component (B) is solid or semi-solid at 25° C., and it does not include higher alcohol. The term "solid or semi-solid at 25° C." is used herein to mean that the viscosity at 25° C. is higher than 10,000 mPa·s. The viscosity is measured in the same manner as that in the case of the component (A).

The oil agent which is solid at 25° C. is not limited, as long as it is generally used for cosmetic compositions. As ester wax, animal wax, plant wax and the like can be used. As hydrocarbon wax, mineral wax, synthetic wax and the like can be used. More specifically, examples of the ester wax include rice bran wax, carnauba wax, candelilla wax, beeswax, and spermaceti. Examples of the hydrocarbon wax include ceresin, paraffin wax, microcrystalline wax, polyethylene wax, and polyolefin wax.

Among these waxes, from the viewpoint of the effect of diminishing skin color unevenness, hydrocarbon waxes are preferable. In addition, waxes having a melting point of 50° C. to 110° C. are preferable, waxes having a melting point of 65° C. to 110° C. are more preferable, and waxes having a melting point of 70° C. to 90° C. are even more preferable.

With regard to the oil agent which is solid at 25° C., commercially available products can be used. For example, Ceresin #810K (melting point: 72° C. to 76° C., manufactured by Nikko Rica Corporation) can be used as ceresin. HNP-9 (melting point: 70° C. to 78° C., manufactured by Nippon Seiro Co., Ltd.) can be used as paraffin wax. Super White Protopet (melting point: 55° C. to 60° C., manufactured by Sonneborn, LLC) can be used as Vaseline. Carnauba Wax (melting point: 80° C. to 86° C., manufactured by Miki Chemical Industry & Co., Ltd.) can be used as carnauba wax. Candelilla Wax (melting point: 68° C. to 72° C., manufactured by Miki Chemical Industry & Co., Ltd.) can be used as candelilla wax. Multiwax W-445 (melting point 76° C. to 82° C., manufactured by Sonneborn, LLC) can be used as microcrystalline wax. PERFORMALENE 655 (melting point: 95° C. to 105° C., manufactured by NEW PHASE TECHNOLOGIES) can be used as polyethylene wax. PERFORMALENE 700EP (melting point: 85° C. to 105° C., manufactured by NEW PHASE TECHNOLOGIES) can be used as polyolefin wax. Golden Brand (melting point: 62° C. to 67° C., manufactured by Miki Chemical Industry & Co., Ltd.) can be used as beeswax.

Examples of the oil agent which is semi-solid at 25° C. include: cholesterol derivatives, such as cholesteryl isostearate, cholesteryl hydroxystearate, macadamia nut oil fatty acid cholesteryl, and di(cholesteryl behenyl octyldodecyl) N-lauroyl-L-glutamate; phytosterol derivatives, such as di(phytosteryl behenyl 2-octyldodecyl) N-lauroyl-L-glutamate, di(phytosteryl 2-octyldodecyl) N-lauroyl-L-glutamate, phytosteryl isostearate, and phytosteryl oleate; dipentaerythritol fatty acid esters, such as dipentaerythritol hexaoxystearate and dipentaerythritol rosinate; triglycerides such as tri(caprylic capric myristic stearic acid)glyceride; and partially hydrogenated triglycerides such as hydrogenated oil; and lanolin, lanosterol derivatives, and Vaseline.

As component (B), from the viewpoint of the diminishment of skin color unevenness, carnauba wax, candelilla wax, beeswax, ceresin, paraffin wax, microcrystalline wax, polyethylene wax, polyolefin wax, and Vaseline are preferable. Among others, ceresin, paraffin wax, microcrystalline wax, polyethylene wax, polyolefin wax and Vaseline are more preferable, and further, ceresin, paraffin wax, microcrystalline wax, polyethylene wax and polyolefin wax are even more preferable.

As such a component (B), one or two or more components can be used in combination. From the viewpoints of the diminishment of skin color unevenness and prevention of stickiness, the content of the component (B) is 1% by mass or more, preferably 2% by mass or more, and more preferably 3% by mass or more, based on the total mass of the entire composition. Also, the content of the component (B) is 6% by mass or less, preferably 5% by mass or less, and more preferably 4% by mass or less, based on the total mass of the entire composition. Moreover, the content of the component (B) from is 1 to 6% by mass, preferably from 2 to 5% by mass, and more preferably from 3 to 4% by mass, based on the entire composition.

From the viewpoints of the diminishment of skin color unevenness and prevention of stickiness, in the skin cosmetic composition of the present invention, the mass ratio of the component (B) to the component (A), (B)/(A), is 0.3 or more, preferably 0.4 or more, and more preferably 0.45 or more, and the mass ratio (B)/(A) is also 1.0 or less, preferably 0.6 or less, and more preferably 0.5 or less. Moreover, the mass ratio of the component (B) to the component (A), (B)/(A), is from 0.3 to 1.0, preferably from 0.4 to 0.6, and more preferably from 0.45 to 0.5.

The alcohol as component (C) is linear alcohol having 12 to 22 carbon atoms, and preferably 14 to 18 carbon atoms. By using the component (C), the component (C) forms a complex with the after-mentioned surfactant as component (D), and as a result, aggregation of the components (A) and (B) can be suppressed during application and drying processes.

Examples of the component (C) include myristyl alcohol, cetyl alcohol, stearyl alcohol, and behenyl alcohol. Among these substances, cetyl alcohol, stearyl alcohol and behenyl alcohol are preferable, and cetyl alcohol and stearyl alcohol are more preferable.

As such a component (C), one or two or more components can be used in combination. From the viewpoints of stability at a high temperature, no stickiness, and the improvement of usability, the content of the component (C) is 0.7% by mass or more, preferably 1.3% by mass or more, and more preferably 1.5% by mass or more, and the content of the component (C) is 3.5% by mass or less, preferably 2.7% by mass or less, and more preferably 2% by mass or less, based on the entire composition. Moreover, the content of the component (C) is from 0.7 to 3.5% by mass, preferably from 1.3 to 2.7% by mass, and more preferably from 1.5 to 2% by mass, based on the entire composition.

The component (D) is an ionic surfactant and/or a nonionic surfactant having an HLB of 12.5 to 15.

Among the components (D), the ionic surfactant includes an anionic surfactant and a cationic surfactant.

Examples of the anionic surfactant include: fatty acid salts having 12 to 24 carbon atoms, such as sodium laurate, potassium palmitate, and arginine stearate; alkyl sulfates, such as sodium lauryl sulfate and potassium lauryl sulfate; alkyl ether sulfates such as polyoxyethylene lauryl sulfate triethanolamine; N-acylsarcosine salts such as lauroylsarcosine sodium; fatty acid amide sulfonates, such as sodium N-stearoyl-N-methyl taurate and sodium N-myristoyl-N-methyl taurate; alkyl phosphates such as sodium monostearyl phosphate; polyoxyethylene alkyl ether phosphates, such as sodium polyoxyethylene oleyl ether phosphate and sodium polyoxyethylene stearyl ether phosphate; long-chain sulfosuccinates such as sodium di-2-ethylhexylsulfosuccinate; and long-chain N-acyl glutamates, such as monosodium N-lauroyl glutamate, sodium N-stearoyl-L-glutamate, arginine N-stearoyl-L-glutamate, sodium N-stearoyl glutamate, and sodium N-myristoyl-L-glutamate.

In addition, as a cationic surfactant, a quaternary ammonium salt is preferable. Examples of the cationic surfactant include dicetyl dimethyl ammonium chloride, distearyl dimethyl ammonium chloride, diaralkyl dimethyl ammonium chloride, and dibehenyl dimethyl ammonium chloride. Among these substances, dicetyl dimethyl ammonium chloride, distearyl dimethyl ammonium chloride, and the like are preferable because these substances have affinity for the skin. Commercially available products of these substances include VARISOFT 432 PPG (Evonik Industries AG), VARISOFT TA 100 (Evonik Industries AG), and the like.

Among the components (D), the nonionic surfactant can improve the spreading of a cosmetic composition upon application, and has an HLB of 12.5 to 15. A nonionic surfactant having an HLB of 12.5 to 14 is preferable.

The term "HLB" (Hydrophilic-Lipophilic Balance) is used herein to mean the molecular weight of a hydrophilic group portion based on the total molecular weight of a surfactant. In the case of a nonionic surfactant, such HLB can be obtained according to the formula of Griffin.

The HLB of a mixed surfactant constituted with two or more nonionic surfactants is obtained as follows. That is, the HLB of a mixed surfactant is obtained by adding the HLB values of individual nonionic surfactants and then averaging the obtained value, based on the mixing ratio thereof.

$$\text{Mixed HLB} = \Sigma(\text{HLB}x \times Wx)/\Sigma Wx$$

wherein HLBx represents the HLB value of a nonionic surfactant X, and

Wx represents the mass (g) of the nonionic surfactant X having an HLBx value.

Examples of the nonionic surfactant as component (D) include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene fatty acid ester, polyoxyethylene sorbitan fatty acid ester, polyoxyethylene alkyl ether, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene hydrogenated castor oil fatty acid ester, polyoxyethylene phytostanol ether, polyoxyethylene phytosterol ether, polyoxyethylene cholestanol ether, polyoxyethylene cholesteryl ether, polyoxyalkylene-modified organopolysiloxane, and polyoxyalkylene/alkyl-comodified organopolysiloxane.

Among these substances, polyoxyethylene alkyl ether and polyoxyethylene hydrogenated castor oil are preferable, and further, polyoxyethylene (20) 2-hexyldecyl ether and polyoxyethylene (40) hydrogenated castor oil are more preferable.

As such nonionic surfactants, commercially available products can be used. For example, as polyoxyethylene (20) 2-hexyldecyl ether, Emulgen 1620G (HLB 14, manufactured by Kao Corporation), EMALEX 1620 (HLB 14, manufactured by Nihon Emulsion Co., Ltd.), and the like can be used. As polyoxyethylene (40) hydrogenated castor oil, Emanon CH-40 (HLB 12.5, manufactured by Kao Corporation), and the like can be used.

As component (D), it is preferable to use a cationic surfactant in combination with a nonionic surfactant, from the viewpoints of smoothness and moist feeling obtained after application. Specifically, it is more preferable to use one or two or more cationic surfactants selected from among dicetyl dimethyl ammonium chloride and distearyl dimethyl ammonium chloride, in combination with one or two or more nonionic surfactants selected from among polyoxyethylene alkyl ether and polyoxyethylene hydrogenated castor oil. It is even more preferable to use one or two or more cationic surfactants selected from among dicetyl dimethyl ammonium chloride and distearyl dimethyl ammonium chloride, in combination with one or two or more nonionic surfactants selected from among polyoxyethylene (20) 2-hexyldecyl ether and polyoxyethylene (40) hydrogenated castor oil.

When a cationic surfactant is used in combination with a nonionic surfactant as component (D), from the same viewpoint as described above, the mass ratio (cationic surfactant/nonionic surfactant) is preferably 0.5 or more, more preferably 1.0 or more, even more preferably 1.5 or more, and preferably 5.0 or less, more preferably 3.0 or less, and even more preferably 2.5 or less.

In addition, when a cationic surfactant is used in combination with a nonionic surfactant as component (D), the mass ratio (cationic surfactant/nonionic surfactant) is preferably from 0.5 to 5.0, more preferably from 1.0 to 3.0, and even more preferably from 1.5 to 2.5.

As component (D), one or two or more components can be used in combination. From the viewpoint of the improvement of the stability of an emulsion composition, the content of the component (D) is 0.2% by mass or more, preferably 0.4% by mass or more, more preferably 0.5% by mass or more, and the content of the component (D) is 1% by mass or less, preferably 0.8% by mass or less, and more preferably 0.6% by mass or less, based on the entire composition. Moreover, the content of the component (D) is from 0.2 to 1% by mass, preferably from 0.4 to 0.8% by mass, and more preferably from 0.5 to 0.6% by mass, based on the entire composition.

In the present invention, it is preferable from the viewpoint of the diminishment of skin color unevenness that hydrocarbon oil be used as component (B) in combination, when ester oil is used as component (A), or that hydrocarbon oil be used as component (A) in combination, when ester oil is used as component (B). Moreover, from the viewpoint of smoothness upon application, it is more preferable that ester oil as component (A) and hydrocarbon oil as component (B) be used in combination. By doing so, stable solid particles can be obtained, and thereby the covering power of a cosmetic composition after the application and drying thereof can be improved.

In the skin cosmetic composition of the present invention, oil agents as components (A) and (B) are uniformly dispersed in a composition, and thus, a stable composition can be obtained. In this skin cosmetic composition, the oil agents as components (A) and (B), the component (C), and the component (D) form a complex in a drying process after application of the cosmetic composition to the skin, so that the cosmetic composition can be uniformly dispersed on the skin without aggregation and thus it can tightly adhere to the skin. Moreover, in the makeup coating film obtained after drying, the complex formed with the oil agents as components (A) and (B), the component (C), and the component (D) is converted to fine particles, and these fine particles then form asperities on the surface of the coating film, thereby obtaining a frosted glass-like coating film. As a result, covering power for diminishing skin color unevenness can be imparted.

From the viewpoint of the spreadability of a cosmetic composition upon application, the content of water as component (E) is preferably 65% by mass or more, and more preferably 70% by mass or more, and preferably 85% by mass or less, and more preferably 80% by mass or less, based on the entire composition. Moreover, the content of the water is preferably from 65 to 85% by mass, and more preferably from 70 to 80% by mass, based on the entire composition.

The skin cosmetic composition of the present invention may further comprise a water-soluble solvent having a refractive index of 1.46 to 1.55, and preferably of 1.47 to 1.50, as component (F). The component (F) can diminish skin color unevenness because it is not sticky and increases surface reflection.

The refractive index is measured at 25° C., using PAL-RI Refractometer manufactured by Atago Co., Ltd.

The water-soluble solvent as component (F) is an aqueous component which is liquid at ordinary temperature. Examples of such a water-soluble solvent include polyoxybutylene polyoxyethylene polyoxypropylene glyceryl ether, polyoxyethylene alkyl glucoside, and polyglycerin. More specific examples include polyoxybutylene polyoxyethylene polyoxypropylene glyceryl ether (3B.O.) (8E.O.) (5P.O.) (refractive index: 1.46), polyoxyethylene methyl glucoside (refractive index: 1.47), and diglycerin (refractive index: 1.48). Among these substances, polyoxyethylene methyl glucoside is more preferable in terms of small level of stickiness, and as a commercially available product, MACBIOBRIDE MG-20E (MS) (manufactured by NOF Corporation) and the like can be used.

As component (F), one or two or more components can be used. From the viewpoints of no stickiness and excellent usability, the content of the component (F) is preferably 0.5% by mass or more, more preferably 0.75% by mass or more, and even more preferably 1% by mass or more, and preferably 3% by mass or less, more preferably 2.5% by mass or less, and even more preferably 2% by mass or less, based on the entire composition. Moreover, the content of the component (F) is preferably from 0.5 to 3% by mass, more preferably from 0.75 to 2.5% by mass, and even more preferably from 1 to 2% by mass, based on the entire composition.

The skin cosmetic composition of the present invention may further comprise (G) one or more compounds selected from among ceramide and a ceramide analog. The use of the compound(s) (G) can improve stability, and particularly, stability at a high temperature.

Examples of such ceramide include those extracted and purified from animals and plants, and those synthesized according to a microbiological method or a scientific method. An example of such ceramide is an amide derivative represented by the following general formula (1):

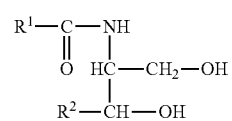

wherein $R^1$ represents a linear or branched, and saturated or unsaturated hydrocarbon group having 8 to 50 carbon atoms, which is optionally substituted with one or more hydroxy groups, or a group represented by $R^3$—COO—$R^4$— (wherein $R^3$ represents a linear or branched, and saturated or unsaturated hydrocarbon group having 8 to 30 carbon atoms, and $R^4$ represents a linear or branched, and saturated or unsaturated, divalent hydrocarbon group having 8 to 40 carbon atoms, which is optionally substituted with one or more hydroxy groups); and $R^2$ represents a linear or branched, and saturated or unsaturated hydrocarbon group having 8 to 50 carbon atoms, which is optionally substituted with one or more hydroxy groups.

Specific examples of the ceramide include ceramides type I to VII, which are described in Robson K. J. et al., J. Lipid Res., 35, 2060 (1994), Wertz P. W. et al., J. Lipid Res., 24, 759 (1983), etc.

Commercially available ceramides, which can be used herein, include Ceramide III, Ceramide IIIB, Ceramide IIIA, Ceramide IV, Phytoceramide I (all of which are manufactured by Degussa), Ceramide II (Sederma), and Ceramide TIC-001 (Takasago International Corporation).

On the other hand, an example of the ceramide analog is an amide derivative represented by the following general formula (2):

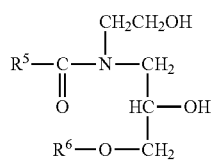

(2)

wherein $R^5$ represents a linear or branched, and saturated or unsaturated hydrocarbon group having 9 to 25 carbon atoms; and $R^6$ represents a linear or branched, and saturated or unsaturated hydrocarbon group having 10 to 26 carbon atoms.

The amide derivative represented by the general formula (2) can be produced by methods described in JP-A-62-228048, JP-A-63-228048, etc. A specific example of the amide derivative is N-(hexadesiloxyhydroxypropyl)-N-hydroxyethyl hexadecanamide, and Sphingolipid E (manufactured by Kao Corporation) or the like can be used.

As component (G), one or two or more components can be used in combination. From the viewpoint of stability, and particularly, stability at a high temperature, the content of the component (G) is preferably 1% by mass or more, more preferably 1.5% by mass or more, and even more preferably 2% by mass or more and preferably 3% by mass or less, more preferably 2.5% by mass or less, and even more preferably 2.25% by mass or less, based on the entire composition. Moreover, the content of the component (G) is preferably from 1 to 3% by mass, more preferably from 1.5 to 2.5% by mass, and even more preferably from 2 to 2.25% by mass, based on the entire composition.

The skin cosmetic composition of the present invention may comprise other components used in ordinary cosmetic compositions, as well as the above described components. Examples of such other components include nonionic surfactants other than those described above, lower alcohol, a moisturizing agent, a water-soluble polymer, an antioxidant, an antiseptic, a chelating agent, a fragrance, a whitening agent, vitamins, and other various medicinal components.

From the viewpoint of the achievement of a natural covering power by a makeup coating film, it is preferable that the skin cosmetic composition of the present invention do not comprise powders.

From the same viewpoint as described above, the content of powders in the present skin cosmetic composition is preferably 2% by mass or less, more preferably 1% by mass or less, even more preferably 0.5% by mass or less, and still more preferably 0.1% by mass or less. It is further preferable that the content of such powders be substantially 0% by mass.

The skin cosmetic composition of the present invention can be produced in the form of an oil-in-water emulsion cosmetic composition according to a method comprising the following steps:

(step 1) a step of heating an oil phase comprising the components (A) to (D) and (G) and other oil agent components at a range between a melting point of a component having the highest melting point among the components and a temperature which is 10° C. higher than the melting point, and then stirring the oil phase to obtain a mixture (1), (step 2) a step of mixing the components (E) and (F) and other water-soluble components, then heating the obtained mixture at a range between a melting point of a component having the highest melting point among the components in the mixture (1) and a temperature which is 10° C. higher than the melting point, and then mixing the thus heated mixture with the mixture (1) that has been heated at the range between the melting point of the component having the highest melting point among the components and the temperature which is 10° C. higher than the melting point, whereby a mixture (2) is obtained, and (step 3) a step of cooling the mixture (2) to a temperature of 15° C. to 35° C.

In the step 2, when the components (E) and (F) and other water-soluble components are mixed with the mixture (1), an impeller, such as a disperser, a homogenizer or a propeller, is used, and the diameter of an emulsion particle can be regulated by controlling a stirring rate and a stirring time. For instance, when a stirring rate is kept constant, the particle diameter can be reduced, as a stirring time is prolonged.

In the mixing of the components (E) and (F) and other water-soluble components with the mixture (1) in the (step 2), from the viewpoints of the after-mentioned emulsion particle diameter which is determined to be a specific value and the diminishment of skin color unevenness, the input energy (kJ/m$^3$) calculated from the stirring rate and the stirring time of an impeller is preferably 10 kJ/m$^3$ or more, more preferably 40 kJ/m$^3$ or more, and even more preferably 100 kJ/m$^3$ or more, and preferably 9,000 kJ/m$^3$ or less, more preferably 1,000 kJ/m$^3$ or less, and even more preferably 300 kJ/m$^3$ or less. Moreover, in the mixing in the (step 2), the input energy (kJ/m$^3$) calculated from the stirring rate and the stirring time of an impeller is preferably from 10 to 9,000 kJ/m$^3$, more preferably from 40 to 1,000 kJ/m$^3$, and even more preferably from 100 to 300 kJ/m$^3$.

The term "input energy" is used herein to mean a value calculated according to the following expression (I):

$$\text{Input energy} = \frac{\rho N p n^3 d^5}{V} t [J/m^3] \quad (I)$$

wherein $\rho$ represents the density of the oil-in-water emulsion skin cosmetic composition, Np represents the power number of an impeller during stirring, n represents the rotation number of the impeller per unit time, d represents the diameter of the impeller, V represents the volume of the oil-in-water emulsion skin cosmetic composition, and t represents a stirring time.

In the production for product of the present invention, an oil-in-water emulsion skin cosmetic composition is produced under conditions in which the oil-in-water emulsion skin cosmetic composition is in a turbulent state, when it is stirred. If the oil-in-water emulsion skin cosmetic composition is in a turbulent state, the value of Np in the above expression (I) would become a constant value, depending on the type of an impeller used. Thus, the calculation was carried out with an Np value of 0.2 when a disperser was used, with an Np value of 0.85 when a homomixer was used, and with an Np value of 0.3 when a propeller was used. In addition, the density of an oil-in-water emulsion skin cosmetic composition, represented by p, was set at 1.

When a composition is produced by setting the total amount thereof at 1 kg using a 2-L beaker, for example, the mixing operation in the (step 2) is carried out at 1,400 to 8,000 rpm for 0.25 to 20 minutes, employing a disperser (T. K. ROBOMICS, PRIMIX).

For the cooling operation included in the step 3, a bulkhead-type heat exchanger or the like can be used. Moreover, from the viewpoint of cooling by uniform stirring, it is desired to perform the cooling operation in combination with a mixing device. Examples of the mixing device, which can be used herein, include high-speed shearing mixing devices such as a disperser and a homogenizer, a stator blade mixer, a rotation-type stirring mixing device, and an oscillating-type stirring mixing device. From the viewpoints of cooling by uniform stirring and the improvement of stability, an oscillating-type stirring mixing device is preferable. Example of the oscillating-type stirring mixing device includes a tubular flow type mixing device and a batch type mixing device. From the viewpoint of an increase in the cooling rate, a tubular flow type mixing device is preferable. As such a tubular-flow oscillating-type stirring mixing device, VIBRO MIXER (manufactured by REICA Co., Ltd.) can be used, for example. Further, from the viewpoints of cooling by uniform stirring and the improvement of stability, the cooling rate is set at 1° C./min or more, and preferably at 30° C./min or more.

From the viewpoint of the diminishment of skin color unevenness, with regard to the oil-in-water emulsion skin cosmetic composition of the present invention, emulsion particles have a number-average particle diameter of 1.0 to 3.0 µm, and preferably of 1.5 to 2.5 µm. The diameter of an emulsion particle can be regulated by controlling the stirring rate and the stirring time, as described above.

The particle diameter of an emulsion particle can be obtained by diluting a cosmetic composition twice with purified water, then dispersing the resulting solution with ultrasonic waves for 60 seconds, and then measuring a number-average particle diameter using a laser diffraction particle size analyzer.

The skin cosmetic composition of the present invention can be used as a skin care cosmetic composition such as foundation, makeup base, UV emulsion, tint emulsion or lip cream. The present skin cosmetic composition can be applied in a dosage form such as lotion, cream, emulsion, beauty essence or skin lotion.

The oil-in-water emulsion skin cosmetic composition of the present invention is applied onto the skin, so as to adjust the appearance of the skin.

Moreover, the oil-in-water emulsion skin cosmetic composition of the present invention is preferably applied onto the skin other than the scalp, so as to adjust the appearance of the skin.

Furthermore, the oil-in-water emulsion skin cosmetic composition of the present invention is preferably applied onto the skin other than the scalp, so as to diminish skin color unevenness.

With regard to the aforementioned embodiment, the present invention further discloses the following composition.

<1> An oil-in-water emulsion skin cosmetic composition comprising the following components (A), (B), (C), (D) and (E):
(A) from 1% to 10% by mass of an oil agent which is liquid at 25° C.,
(B) from 1% to 6% by mass of an oil agent which is solid or semi-solid at 25° C.,
(C) from 0.7% to 3.5% by mass of linear alcohol having 12 to 22 carbon atoms,
(D) from 0.2% to 1% by mass of at least one selected from the group consisting of an ionic surfactant and a nonionic surfactant having an HLB of 12.5 to 15, and
(E) water, wherein
the mass ratio of the component (B) to the component (A), (B)/(A), is from 0.3 to 1.0, and
emulsion particles have a number-average particle diameter of 1.0 to 3.0 µm.

<2> The oil-in-water emulsion skin cosmetic composition according to <1> above, wherein the component (A) is preferably ester oil, more preferably at least one selected from the group consisting of isononyl isononanoate, isotridecyl isononanoate, octyl dodecyl myristate, isopropyl palmitate, isopropyl isostearate, butyl stearate, myristyl myristate, isopropyl myristate, octyl dodecyl myristate, neopentyl glycol dicaprate, tricaproin, pentaerythrityl 2-ethylhexanoate, meadowfoam oil and olive oil, and even more preferably at least one selected from the consisting of olive oil, neopentyl glycol dicaprate, and isotridecyl isononanoate.

<3> The oil-in-water emulsion skin cosmetic composition according to <1> or <2> above, wherein the content of the component (A) is preferably 3% by mass or more, more preferably 5% by mass or more, preferably 8% by mass or less, and more preferably 7% by mass or less, based on the entire composition, and wherein the content of the component (A) is preferably from 3 to 8% by mass, and more preferably from 5 to 7% by mass, based on the entire composition.

<4> The oil-in-water emulsion skin cosmetic composition according to any one of <1> to <3> above, wherein the component (B) is preferably an oil agent having a melting point of 65° C. to 110° C., and more preferably an oil agent having a melting point of 70° C. to 90° C.

<5> The oil-in-water emulsion skin cosmetic composition according to any one of <1> to <4> above, wherein the component (B) is preferably carnauba wax, candelilla wax, beeswax, ceresin, paraffin wax, microcrystalline wax, polyethylene wax, polyolefin wax or Vaseline, more preferably ceresin, paraffin wax, microcrystalline wax, polyethylene wax, polyolefin wax or Vaseline, and even more preferably ceresin, paraffin wax, microcrystalline wax, polyethylene wax or polyolefin wax.

<6> The oil-in-water emulsion skin cosmetic composition according to any one of <1> to <5> above, wherein the content of the component (B) is preferably 2% by mass or more, more preferably 3% by mass or more, preferably 5% by mass or less, and more preferably 4% by mass or less, based on the entire composition, and wherein the content of the component (B) is preferably from 2 to 5% by mass, and more preferably from 3 to 4% by mass, based on the entire composition.

<7> The oil-in-water emulsion skin cosmetic composition according to any one of <1> to <6> above, wherein the mass ratio of the component (B) to the component (A), (B)/(A), is preferably 0.4 or more, more preferably 0.45 or more, preferably 0.6 or less, and more preferably 0.5 or less, and wherein the mass ratio (B)/(A) between the components (A) and (B) is preferably from 0.4 to 0.6, and more preferably from 0.45 to 0.5.

<8> The oil-in-water emulsion skin cosmetic composition according to any one of <1> to <7> above, wherein the component (C) is preferably linear alcohol having 14 to 18 carbon atoms, and more preferably cetyl alcohol or stearyl alcohol.

<9> The oil-in-water emulsion skin cosmetic composition according to any one of <1> to <8> above, wherein the content of the component (C) is preferably 1.3% by mass or more, more preferably 1.5% by mass or more, preferably 2.7% by mass or less, and more preferably 2% by mass or less, based on the entire composition, and wherein the content of the component (C) is preferably from 1.3 to 2.7% by mass, and more preferably from 1.5 to 2% by mass, based on the entire composition.

<10> The oil-in-water emulsion skin cosmetic composition according to any one of <1> to <9> above, wherein the component (D) is preferably an ionic surfactant, more preferably an anionic surfactant or a cationic surfactant, and even more preferably dicetyl dimethyl ammonium chloride or distearyl dimethyl ammonium chloride.

<11> The oil-in-water emulsion skin cosmetic composition according to any one of <1> to <9> above, wherein the component (D) is preferably a nonionic surfactant, more preferably a nonionic surfactant having an HLB of 12.5 to 15, and even more preferably a nonionic surfactant having an HLB of 12.5 to 14, wherein the nonionic surfactant is preferably polyoxyethylene alkyl ether or polyoxyethylene hydrogenated castor oil.

<12> The oil-in-water emulsion skin cosmetic composition according to any one of <1> to <11> above, wherein the component (D) is preferably a combination of a cationic surfactant with a nonionic surfactant, more preferably a combination of at least one cationic surfactant selected from the group consisting of dicetyl dimethyl ammonium chloride and distearyl dimethyl ammonium chloride, with at least one nonionic surfactant selected from the group consisting of polyoxyethylene alkyl ether and polyoxyethylene hydrogenated castor oil, and even more preferably a combination of at least one cationic surfactant selected from the group consisting of dicetyl dimethyl ammonium chloride and distearyl dimethyl ammonium chloride, with one or two or at least one surfactant selected from the group consisting of polyoxyethylene (20) 2-hexyldecyl ether and polyoxyethylene (40) hydrogenated castor oil.

<13> The oil-in-water emulsion skin cosmetic composition according to any one of <1> to <12> above, wherein the component (D) preferably comprises a cationic surfactant and a nonionic surfactant, and the mass ratio between the cationic surfactant and the nonionic surfactant (cationic surfactant/nonionic surfactant) is preferably 0.5 or more, more preferably 1.0 or more, even more preferably 1.5 or more, preferably 5.0 or less, more preferably 3.0 or less, and even more preferably 2.5 or less.

<14> The oil-in-water emulsion skin cosmetic composition according to any one of <1> to <13> above, wherein the content of the component (D) is preferably 0.4% by mass or more, more preferably 0.5% by mass or more, preferably 0.8% by mass or less, and more preferably 0.6% by mass or less, based on the entire composition, and wherein the content of the component (D) is preferably from 0.4 to 0.8% by mass, and more preferably from 0.5 to 0.6% by mass, based on the entire composition.

<15> The oil-in-water emulsion skin cosmetic composition according to any one of <1> to <14> above, wherein when ester oil is used as component (A), hydrocarbon oil is preferably used as component (B) in combination, or when ester oil is used as component (B), hydrocarbon oil is preferably used as component (A) in combination.

<16> The oil-in-water emulsion skin cosmetic composition according to any one of <1> to <15> above, wherein the content of water as component (E) is preferably 65% by mass or more, more preferably 70% by mass or more, preferably 85% by mass or less, and more preferably 80% by mass or less, based on the entire composition, and wherein the content of the water is preferably from 65 to 85% by mass, and more preferably from 70 to 80% by mass, based on the entire composition.

<17> The oil-in-water emulsion skin cosmetic composition according to any one of <1> to <16> above, which further comprises (F) a water-soluble solvent having a refractive index of preferably 1.46 to 1.55, and more preferably 1.47 to 1.50.

<18> The oil-in-water emulsion skin cosmetic composition according to <17> above, wherein the water-soluble solvent as component (F) is preferably polyoxybutylene polyoxyethylene polyoxypropylene glyceryl ether, polyoxyethylene alkyl glucoside or polyglycerin, and more preferably polyoxybutylene polyoxyethylene polyoxypropylene glyceryl ether (3B.O.) (8E.O.) (5P.O.) (refractive index: 1.46), polyoxyethylene methyl glucoside (refractive index: 1.47) or diglycerin (refractive index: 1.48).

<19> The oil-in-water emulsion skin cosmetic composition according to <17> or <18> above, wherein the content of the component (F) is preferably 0.5% by mass or more, more preferably 0.75% by mass or more, even more preferably 1% by mass or more, preferably 3% by mass or less, more preferably 2.5% by mass or less, and even more preferably 2% by mass or less, based on the total mass of the entire composition, and wherein the content of the component (F) is preferably from 0.5 to 3% by mass, more preferably from 0.75 to 2.5% by mass, and even more preferably from 1 to 2% by mass, based on the entire composition.

<20> The oil-in-water emulsion skin cosmetic composition according to any one of <1> to <19> above, which preferably further comprises (G) one or more compounds selected from the group consisting of ceramide and ceramide analogs.

<21> The oil-in-water emulsion skin cosmetic composition according to <20> above, wherein the component (G) is preferably an amide derivative represented by the following general formula (1):

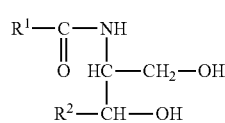

(1)

wherein $R^1$ represents a linear or branched, and saturated or unsaturated hydrocarbon group having 8 to 50 carbon atoms, which is optionally substituted with one or more hydroxy groups, or a group represented by $R^3$—COO—$R^4$— (wherein $R^3$ represents a linear or branched, and saturated or unsaturated hydrocarbon group having 8 to 30 carbon atoms, and $R^4$ represents a linear or branched, and saturated or unsaturated, divalent hydrocarbon group having 8 to 40 carbon atoms, which is optionally substituted with one or more hydroxy groups); and $R^2$ represents a linear or branched, and saturated or unsaturated hydrocarbon group having 8 to 50 carbon atoms, which is optionally substituted with one or more hydroxy groups, or an amide derivative represented by the following general formula (2):

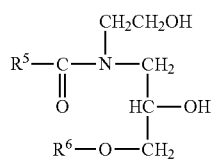

(2)

wherein $R^5$ represents a linear or branched, and saturated or unsaturated hydrocarbon group having 9 to 25 carbon atoms; and $R^6$ represents a linear or branched, and saturated or unsaturated hydrocarbon group having 10 to 26 carbon atoms.

<22> The oil-in-water emulsion skin cosmetic composition according to <20> or <21> above, wherein the content of the component (G) is preferably 1% by mass or more, more preferably 1.5% by mass or more, even more preferably 2% by mass or more, preferably 3% by mass or less, more preferably 2.5% by mass or less, and even more preferably 2.25% by mass or less, based on the entire composition, and wherein the content of the component (G) is preferably from 1 to 3% by mass, more preferably from 1.5 to 2.5% by mass, and even more preferably from 2 to 2.25% by mass, based on the entire composition.

<23> The oil-in-water emulsion skin cosmetic composition according to any one of <1> or <22> above, wherein the content of powders in the skin cosmetic composition is preferably 2% by mass or less, more preferably 1% by mass or less, even more preferably 0.5% by mass or less, still more preferably 0.1% by mass or less, and further more preferably, substantially 0% by mass.

<24> The oil-in-water emulsion skin cosmetic composition according to any one of <1> to <23> above, wherein the number-average particle diameter of emulsion particles is preferably from 1.5 to 2.5 μm.

<25> A method for adjusting the appearance of skin, which comprises applying the oil-in-water emulsion skin cosmetic composition according to any one of <1> to <24> above to the skin, and preferably to the skin other than the scalp.

<26> A method for diminishing skin color unevenness, which comprises applying the oil-in-water emulsion skin cosmetic composition according to any one of <1> to <24> above to the skin, and preferably to the skin other than the scalp.

<27> A method for producing the oil-in-water emulsion skin cosmetic composition according to any one of <1> to <24> above, which comprises the following steps:
(step 1) a step of heating an oil phase comprising the components (A) to (D) and (G) and other oil agent components at a range between a melting point of a component having the highest melting point among the components and a temperature which is 10° C. higher than the melting point, and then stirring the oil phase to obtain a mixture (1),
(step 2) a step of mixing the components (E) and (F) and other water-soluble components, then heating the obtained mixture at a range between a melting point of a component having the highest melting point among the components in the mixture (1) and a temperature which is 10° C. higher than the melting point, and then mixing the thus heated mixture with the mixture (1) that has been heated at the range between the melting point of the component having the highest melting point among the components in the mixture (1) and the temperature which is 10° C. higher than the melting point, whereby a mixture (2) is obtained, and
(step 3) a step of cooling the mixture (2) to a temperature of 15° C. to 35° C.

<28> The method for producing the oil-in-water emulsion skin cosmetic composition according to <27> above, wherein, during the components (E) and (F) and other water-soluble components are mixed with the mixture (1) in the step (2), the input energy (kJ/m$^3$) calculated from the stirring rate and the stirring time of an impeller is preferably 10 kJ/m$^3$ or more, more preferably 40 kJ/m$^3$ or more, even more preferably 100 kJ/m$^3$ or more, preferably 9,000 kJ/m$^3$ or less, more preferably 1,000 kJ/m$^3$ or less, and even more preferably 300 kJ/m$^3$ or less.

<29> The method for producing the oil-in-water emulsion skin cosmetic composition according to <27> or <28> above, wherein the cooling operation included in the step 3 is preferably carried out by cooling the mixture (2) with a cooling device at a rate of 1° C./min or more, and more preferably carried out by using an oscillating-type stirring mixing device as the cooling device, supplying the mixture (2) by using a proportioning pump, and then continuously cooling at a rate of 30° C./min or more in the device, while stirring.

EXAMPLES

Examples 1 to 22 and Comparative Examples 1 to 11

1 kg of each of the oil-in-water emulsion skin cosmetic compositions having the compositions shown in Table 1 and Table 2 was produced. The diameter of an emulsion particle was measured, and at the same time, the diminishment of skin color unevenness (covering power), no stickiness, preservation stability, smoothness and moist feeling were evaluated. The results are also shown in Table 1 and Table 2.
(Production Method)
Step 1:
An oil phase comprising the components (A) to (D) and (G) and other oil agent components was heated at a range between a melting point of a component having the highest melting point among the components and a temperature which was 10° C. higher than the melting point, and the oil phase was then stirred to obtain a mixture (1).
Step 2:
The components (E) and (F) and other water-soluble components were mixed with one another, and the obtained mixture was then heated at a range between a melting point of a component having the highest melting point among the components in the mixture (1) and a temperature which was 10° C. higher than the melting point. The thus heated mixture was further mixed with the mixture (1) that had been heated at the range between the melting point of the component having the highest melting point among the components in the mixture (1) and the temperature which is 10° C. higher than the melting point, whereby a mixture (2) was obtained.

When the water-soluble components comprising the components (E) and (F) was mixed with the mixture (1), the mixing operation was carried out using a disperser (manufactured by PRIMIX Corporation, ultra-high speed multi-stirring system ROBOMIX (registered trademark)) at a stirring rate of 1,400 to 8,000 rpm for a stirring time of 0.25 to 20 minutes.

Step 3:

The mixture (2) was cooled to a temperature of 15° C. to 35° C., so as to obtain an oil-in-water emulsion skin cosmetic composition.

It is to be noted that the diameter of an emulsion particle in each of the oil-in-water emulsion skin cosmetic compositions of Examples 1 to 22 was adjusted to a predetermined size by controlling a stirring rate and a stirring time applied to the disperser used in the step 2. Tables 1 and 2 show the stirring rate and the stirring time applied to the disperser and the power calculated according to the above expression (I).

On the other hand, in Comparative Examples 1 to 7, and 11, oil-in-water emulsion skin cosmetic compositions were each produced at a stirring rate of 4,000 rpm for a stirring time of 3 minutes, which were applied to the disperser. In Comparative Example 8, an oil-in-water emulsion skin cosmetic composition was produced at a stirring rate of 8,000 rpm for a stirring time of 60 minutes, which were applied to the disperser. In Comparative Example 9, an oil-in-water emulsion skin cosmetic composition was produced at a stirring rate of 1,400 rpm for a stirring time of 0.2 minutes, which were applied to the disperser.

(Evaluation Method)

(1) Measurement of Particle Diameter:

Each cosmetic composition was diluted twice with purified water, and the resulting solution was then dispersed with ultrasonic waves for 60 seconds. Thereafter, the diameter of an emulsion particle was measured using a laser diffraction particle size analyzer SALD-2100 (manufactured by Shimadzu Corporation), and the emulsion particle diameter was obtained as a number-average particle diameter.

(2) Diminishment of Skin Color Unevenness (Covering Power) ($\Delta Y$):

According to the configuration of Example 1 of JP-A-2012-217790, an artificial skin with a diameter of 5 cm was obtained. An uneven brown color component with a diameter of 5 mm (as described later) was applied to the center of the artificial skin, so as to produce an artificial skin used for evaluation. This uneven color component portion and a portion having no such color unevenness were each measured using Color-Difference Meter CM2600D (manufactured by Konica Minolta Inc.), and luminance (Y value) was obtained. An uneven color model was prepared such that a luminance difference ($\Delta Y$) of 5 could be achieved.

0.1 g of each cosmetic composition was uniformly applied onto the upper surface as a whole of this uneven color model, and immediately after the application of the cosmetic composition, the uneven color component portion and the portion without such color unevenness were each measured in terms of luminance (Y value). Then, a difference ($\Delta Y$) was calculated. As the value ($\Delta Y$) decreases, color unevenness is diminished (covering power becomes greater).

(Method for Producing Uneven Brown Color Component)

Polytetramethylene glycol was mixed with naphthalene diisocyanate at a ratio of 1:1, and a pigment (red iron oxide: approximately 0.3 parts by mass; yellow iron oxide: approximately 0.1 part by mass; black iron oxide: approximately 0.01 part by mass; and titanium oxide: approximately 2.08 parts by mass) was further added thereto in an amount of 2.5% by mass with respect to this resin as a whole, and the thus obtained mixture was uniformly blended. Thereafter, the obtained mixture was stirred under a reduced pressure for approximately 3 minutes, and air bubbles were then removed, so as to obtain an uneven brown color component.

(3) No Stickiness:

0.3 g of each cosmetic composition was applied to the face, and no stickiness to the cheek was then subjected to sensory evaluation by 10 trained panelists. The results were shown using the number of the panelists who evaluated the cosmetic composition as "no stickiness."

(4) Preservation Stability:

30 g of each cosmetic composition was placed in a 50-mL transparent screw tube, and it was then preserved at a room temperature for 1 month, or in a thermostatic chamber at 50° C. for 1 month. Thereafter, the appearance of each cosmetic composition was observed by visual confirmation. A cosmetic composition, which was uniform and was not separated, was evaluated to be "b," a cosmetic composition in which a supernatant thereof was slightly clouded was evaluated to be "c," and a cosmetic composition, which was completely separated into two layers, was evaluated to be "d."

(5) Smoothness:

0.15 g of each cosmetic composition was applied to a half of face after face-washing, and it was then dried for 3 minutes. Thereafter, the skin was touched with palms, and the smoothness of the skin felt at that time was compared with the skin of the other half of face to which the cosmetic composition had not been applied. Evaluation was made by 10 trained panelists. The results were shown using the number of the panelists who evaluated the skin, to which the cosmetic composition had been applied, as "being smoother."

(6) Moist Feeling:

0.15 g of each cosmetic composition was applied to a half of face after face-washing, and it was then dried for 3 minutes. Thereafter, the skin was touched with palms, and the moist feeling of the skin obtained at that time was compared with the skin of the other half of face to which the cosmetic composition had not been applied. Evaluation was made by 10 trained panelists. The results were shown using the number of the panelists who evaluated the skin, to which the cosmetic composition had been applied, as "being more moist."

TABLE 1

| Component (% by mass) | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A Olive oil (Cropure OL-LQ-(JP), manufactured by Croda Japan K. K.) | 6.7 | 6.7 | | 6.7 | 6.7 | 6.7 | 6.7 | 6.7 | 6.7 | 6.7 | 6.7 | 6.7 | 6.7 | 6.7 | | | 6.7 |
| Neopentyl glycol dicaprate (Estemol N-01, manufactured by NOF Corporation) | | | 6.7 | | | | | | | | | | | | | 6.7 | |
| Liquid isoparaffin (ParLeam EX, manufactured by the Nisshin OilliO Group, Ltd.) | | | | | | | | | | | | | | | 6.7 | | |
| B Ceresin (melting point: 72° C. to 76° C.) (Ceresin #810K, manufactured by Nikko Rica Corporation) | 1.5 | 1.5 | 1.5 | 1.5 | 1.5 | 1.5 | 1.5 | 1.5 | 1.5 | 1.5 | 1.5 | 1.5 | 1.5 | | 1.5 | 1 | 2 |
| High-melting-point paraffin (melting point: 70° C. to 78° C.) (HNP-9, manufactured by Nippon Seiro Co., Ltd.) | 1.5 | 1.5 | 1.5 | 1.5 | 1.5 | 1.5 | 1.5 | 1.5 | 1.5 | 1.5 | 1.5 | 1.5 | 1.5 | | 1.5 | 1 | 2 |
| Vaseline (melting point: 55° C. to 60° C.) (Super White Protopet, manufactured by Sonneborn, LLC) | | | | | | | | | | | | | | | | | |
| Carnauba wax (melting point: 80° C. to 86° C.) (Carnauba Wax, manufactured by Miki Chemical Industry & Co., Ltd.) | | | | | | | | | | | | | | 1.5 | | | |
| Candelilla wax (melting point: 68° C. to 72° C.) (Candelilla Wax, manufactured by Miki Chemical Industry & Co., Ltd.) | | | | | | | | | | | | | | 1.5 | | | |
| C Stearyl alcohol | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 |
| Cetanol | 0.9 | 0.9 | 0.9 | 0.9 | 0.9 | 0.9 | 0.9 | 0.9 | 0.9 | 0.9 | 0.9 | 0.9 | 0.9 | 0.9 | 0.9 | 0.9 | 0.9 |
| D Distearyl dimethyl ammonium chloride (VARISOFT TA 100, manufactured by Evonik Industries AG) | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 |
| Polyoxyethylene (20) 2-hexyldecyl ether (HLB: 14) (Emulgen 1620G, manufactured by Kao Corporation) | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| F Polyoxybutylene polyoxyethylene polyoxypropylene glyceryl ether (3B.O.) (8E.O.) (5P.O.) (refractive index: 1.46) (WILBRIDE, manufactured by NOF Corporation) | 1 | 1 | 1 | 1 | 1 | 1 | | | 1 | 0.5 | 3 | | | | | | |
| Polyoxyethylene methyl glucoside (refractive index: 1.47) (MACBIOBRIDE MG-20E (MS), manufactured by NOF Corporation) | | | | | | | | | | | | 3 | | | | | |
| Diglycerin (refractive index: 1.48) (Diglycerin, manufactured by Daicel Corporation) | | | | | | | | | | | | | 3 | | | | |
| N-(hexadesiloxyhydroxypropyl)-N-hydroxyethyl hexadecanamide (Sphingolipid E, manufactured by Kao Corporation) | | | | | | | | | | | | | 2 | 1 | 1 | 1 | |
| Glycerin (refractive index: 1.45) | 2 | 2 | 2 | 2 | 2 | 2 | | 2 | | 2 | 2 | 2 | | 2 | 2 | 2 | 2 |
| E Purified water | 75.2 | 75.2 | 75.2 | 75.2 | 75.2 | 75.2 | 78.2 | 76.2 | 77.2 | 75.7 | 73.2 | 73.2 | 73.2 | 75.2 | 75.2 | 76.2 | 74.2 |
| Total | 100 | 100 | 100 | 100 | 100 | 100 | 100 | 100 | 100 | 100 | 100 | 100 | 100 | 100 | 100 | 100 | 100 |
| B/A | 0.45 | 0.45 | 0.45 | 0.45 | 0.45 | 0.45 | 0.45 | 0.45 | 0.45 | 0.45 | 0.45 | 0.45 | 0.45 | 0.45 | 0.45 | 0.30 | 0.60 |
| Cationic surfactant/nonionic surfactant | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| Number-average particle diameter (μm) | 1 | 1.5 | 1.6 | 2 | 2.5 | 3 | 1.5 | 1.5 | 1.5 | 1.5 | 1.5 | 1.5 | 1.5 | 1.7 | 1.5 | 1.5 | 1.6 |
| Diminishment of skin color unevenness (covering power) (ΔY) | 3.9 | 3.8 | 3.8 | 3.5 | 3.8 | 3.9 | 4.0 | 4.0 | 3.8 | 3.9 | 3.6 | 3.7 | 3.5 | 4.2 | 4.2 | 3.9 | 3.8 |
| No stickiness | 10 | 10 | 10 | 10 | 9 | 9 | 9 | 10 | 9 | 10 | 10 | 10 | 10 | 8 | 10 | 10 | 8 |
| Preservation stability: room temperature, 1 month | b | b | b | b | b | b | c | b | b | b | b | b | b | b | b | b | b |
| 50° C., 1 month | 10 | 10 | 10 | 10 | 10 | 10 | 10 | 10 | c | 10 | 10 | 10 | 10 | 10 | 10 | 10 | 10 |
| Smoothness | 10 | 10 | 10 | 10 | 10 | 10 | 10 | 10 | 10 | 10 | 10 | 10 | 10 | 10 | 10 | 10 | 10 |
| Moist feeling | 10 | 10 | 10 | 10 | 10 | 10 | 10 | 10 | 10 | 10 | 10 | 10 | 10 | 10 | 10 | 10 | 10 |
| Rate of disperser (rpm) | 4000 | 4000 | 4000 | 3000 | 1500 | 4000 | 4000 | 4000 | 4000 | 4000 | 4000 | 4000 | 4000 | 4000 | 4000 | 4000 | 4000 |
| Stirring time (min) | 20 | 2 | 1.5 | 0.4 | 0.25 | 0.7 | 3 | 2 | 3 | 2 | 2 | 2 | 2 | 1 | 2 | 2 | 1.5 |
| Input energy [kJ/m³] | 7300 | 730 | 550 | 150 | 40 | 13 | 1090 | 730 | 1090 | 730 | 730 | 730 | 730 | 360 | 730 | 730 | 550 |

TABLE 2

| Component (% by mass) | Example 18 | Example 19 | Example 20 | Example 21 | Example 22 | Comp. 1 | Comp. 2 | Comp. 3 | Comp. 4 | Comp. 5 | Comp. 6 | Comp. 7 | Comp. 8 | Comp. 9 | Comp. 10 | Comp. 11 |
|---|---|---|---|---|---|---|---|---|---|---|---|---|---|---|---|---|
| A Olive oil (Cropure OL-LQ-(JP), manufactured by Croda Japan K.K.) | 6.7 | 6.7 | 10 | 3 | 6.7 |  |  | 6.7 |  | 6.7 | 6.7 | 6.7 | 6.7 | 6.7 | 10 | 2 |
| Neopentyl glycol dicaprate (Estemol N-01, manufactured by the Nisshin OilliO Group, Ltd.) |  |  |  |  |  | 6.7 | 6.7 |  |  |  |  |  |  |  |  |  |
| Liquid isoparaffin (ParLeam EX, manufactured by NOF Corporation) |  |  |  |  |  |  |  |  | 6.7 |  |  |  |  |  |  |  |
| B Ceresin (melting point: 72° C. to 76° C.) (Ceresin #810K, manufactured by Nikko Rica Corporation) | 2.5 | 3 | 1.5 | 1.5 |  | 1.5 |  | 1.5 |  |  | 3.5 | 5 | 1.4 | 1.4 | 0.5 | 1.5 |
| High-melting-point paraffin (melting point: 70° C. to 78° C.) (HNP-9, manufactured by Nippon Seiro Co., Ltd.) | 2.5 | 3 | 1.5 | 1.5 |  | 1.5 |  | 1.5 |  |  | 3.5 | 5 | 1.6 | 1.6 | 0.5 | 1.5 |
| Vaseline (melting point: 55° C. to 60° C.) (Super White Protopet, manufactured by Sonneborn, LLC) |  |  |  |  | 3 |  |  |  |  |  |  |  |  |  |  |  |
| Carnauba wax (melting point: 80° C. to 86° C.) (Carnauba Wax, manufactured by Miki Chemical Industry & Co., Ltd.) |  |  |  |  |  |  |  |  |  |  |  |  |  |  |  |  |
| Candelilla wax (melting point: 68° C. to 72° C.) (Candelilla Wax, manufactured by Miki Chemical Industry & Co., Ltd.) |  |  |  |  |  |  |  |  |  |  |  |  |  |  |  |  |
| C Stearyl alcohol | 0.6 | 0.6 | 0.6 | 0.6 | 0.6 | 0.6 | 0.6 |  | 0.6 |  | 0.6 | 0.6 | 0.6 | 0.6 | 0.6 | 0.6 |
| Cetanol | 0.9 | 0.9 | 0.9 | 0.9 | 0.9 | 0.9 | 0.9 |  | 0.9 |  | 0.9 | 0.9 | 0.9 | 0.9 | 0.9 | 0.9 |
| D Distearyl dimethyl ammonium chloride (VARISOFT TA 100, manufactured by Evonik Industries AG) | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 |
| Polyoxyethylene (20) 2-hexyldecyl ether (HLB: 14) (Emulgen 1620G, manufactured by Kao Corporation) | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| F Polyoxyethylene polyoxybutylene glyceryl ether (3B.O.) (8E.O.) (refractive index: 1.46) (WILBRIDE, manufactured by NOF Corporation) | 1 | 1 | 1 | 1 | 1 | 1 | 1 | 1 | 1 | 1 | 1 | 1 | 1 | 1 | 1 | 1 |
| Polyoxyethylene polyoxypropylene glyceryl ether (5P.O.) |  |  |  |  |  |  |  |  |  |  |  |  |  |  |  |  |
| Polyoxyethylene methyl glucoside (refractive index: 1.47) (MACBIOBRIDE MG-20E (MS), manufactured by NOF Corporation) |  |  |  |  |  |  |  |  |  |  |  |  |  |  |  |  |
| Diglycerin (refractive index: 1.48) (Diglycerin, manufactured by Daicel Corporation) | 2 | 2 | 2 | 2 | 2 | 2 | 2 | 2 | 2 | 2 | 2 | 2 | 2 | 2 | 2 | 2 |
| G N-(hexadesiloxyhydroxypropyl)-N-hydroxyethyl hexadecanamide (Sphingolipid E, manufactured by Kao Corporation) |  |  |  |  |  |  |  |  |  |  |  |  |  |  |  |  |
| Glycerin (refractive index: 1.45) |  |  |  |  |  |  |  |  |  |  |  |  |  |  |  |  |
| E Purified water | 10 | 10 | 10 | 10 | 10 | 10 | 10 | 10 | 10 | 10 | 10 | 10 | 10 | 10 | 10 | 10 |
| | 73.2 | 72.2 | 71.9 | 78.9 | 75.2 | 81.9 | 78.2 | 76.7 | 84.9 | 79.7 | 71.2 | 68.2 | 75.2 | 75.2 | 73.9 | 79.9 |
| Total | 100 | 100 | 100 | 100 | 100 | 100 | 100 | 100 | 100 | 100 | 100 | 100 | 100 | 100 | 100 | 100 |
| B/A | 0.75 | 0.90 | 0.30 | 1.00 | 0.45 | 0.45 | 0.00 | 0.45 | — | — | 1.04 | 1.49 | 0.45 | 0.45 | 0.10 | 1.50 |
| Cationic surfactant/nonionic surfactant | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| Number-average particle diameter (μm) | 1.5 | 1.4 | 1.5 | 1.5 | 1.5 | 1.5 | 1.5 | 1.5 | 1.5 | 1.5 | 1.5 | 1.5 | 0.5 | 4 | 1.5 | 1.5 |
| Diminishment of skin color unevenness (covering power) (ΔY) | 3.7 | 3.7 | 3.8 | 3.7 | 4.3 | 3.8 | 5 | 4.5 | 5.0 | 5.0 | 3.6 | 3.6 | 4.5 | 4.5 | 4.6 | 3.6 |
| No stickiness | 6 | 6 | 10 | 6 | 8 | 1 | 10 | 6 | 10 | 10 | 2 | 0 | 10 | 8 | 10 | 3 |
| Preservation stability: room temperature, 1 month | b | b | b | b | b | b | b | b | b | b | b | b | b | b | b | b |
| 50° C., 1 month | b | b | b | b | b | b | b | b | b | b | b | b | b | b | b | b |
| Smoothness | 10 | 10 | 10 | 10 | 10 | 10 | 10 | 10 | 10 | 10 | 10 | 10 | 10 | 10 | 10 | 10 |
| Moist feeling | 10 | 10 | 10 | 10 | 10 | 10 | 10 | 10 | 10 | 10 | 10 | 10 | 10 | 10 | 10 | 10 |
| Rate of disperser (rpm) | 3500 | 3500 | 3500 | 3500 | 3500 | 4000 | 4000 | 4000 | 4000 | 4000 | 4000 | 8000 | 4000 | 1400 | 4000 | 4000 |
| Stirring time (min) | 3 | 4 | 3 | 3 | 3 | 3 | 3 | 3 | 3 | 3 | 3 | 3 | 60 | 0.2 | 3 | 3 |
| Input energy [kJ/m³] | 730 | 980 | 730 | 730 | 730 | — | — | — | — | — | — | — | — | — | — | — |

Example 23 (Makeup Base)

A makeup base with the below-mentioned composition was produced in the same manner as that of Example 2. The number-average particle diameter of emulsion particles was 1.5 μm.

The produced makeup base could diminish skin color unevenness, could naturally cover the skin color unevenness, had no stickiness, and had excellent usability and good preservation stability.

| (Component) | |
|---|---|
| Olive oil (Cropure OL-LQ-(JP), manufactured by Croda Japan K. K.) | 8.0 (% by mass) |
| Neopentyl glycol dicaprate (Estemol N-01, manufactured by the Nisshin OiliO Group, Ltd.) | 2.0 |
| Ceresin (melting point: 72° C. to 76° C.) (Ceresin #810K, manufactured by Nikko Rica Corporation) | 2.5 |
| High-melting-point paraffin wax (melting point: 70° C. to 78° C.) (HNP-9, manufactured by Nippon Seiro Co., Ltd.) | 2.5 |
| Stearyl alcohol | 1.0 |
| Cetanol | 1.5 |
| Distearyl dimethyl ammonium chloride (VARISOFT TA 100, manufactured by Evonik Industries AG) | 0.6 |
| Polyoxyethylene (20) 2-hexyldecyl ether (HLB: 14) (Emulgen 1620G, manufactured by Kao Corporation) | 0.4 |
| N-(hexadesiloxyhydroxypropyl)-N-hydroxyethyl hexadecanamide (Sphingolipid E, manufactured by Kao Corporation) | 2.0 |
| Glycerin | 5.0 |
| Coloring agent | Trace amount |
| Fragrance | Trace amount |
| Purified water | Balance |
| Total | 100 |

Example 24 (UV Emulsion)

A UV emulsion with the below-mentioned composition was produced in the same manner as that of Example 2. The number-average particle diameter of emulsion particles was 1.5 μm.

The produced UV emulsion could diminish skin color unevenness, could naturally cover the skin color unevenness, had no stickiness, and had excellent usability and good preservation stability.

| (Component) | |
|---|---|
| Olive oil (Cropure OL-LQ-(JP), manufactured by Croda Japan K. K.) | 4.0 (% by mass) |
| Neopentyl glycol dicaprate (Estemol N-01, manufactured by the Nisshin OiliO Group, Ltd.) | 2.0 |
| Uvinul A PLUS B (BASF SE) | 1.5 |
| Uvinul MC80 (BASF SE) | 2.0 |
| Ceresin (melting point: 72° C. to 76° C.) (Ceresin #810K, manufactured by Nikko Rica Corporation) | 1.0 |
| High-melting-point paraffin wax (melting point: 70° C. to 78° C.) (HNP-9, manufactured by Nippon Seiro Co., Ltd.) | 1.0 |
| Stearyl alcohol | 0.9 |
| Cetanol | 1.2 |
| Distearyl dimethyl ammonium chloride (VARISOFT TA 100, manufactured by Evonik Industries AG) | 0.6 |
| Polyoxyethylene (20) 2-hexyldecyl ether (HLB: 14) (Emulgen 1620G, manufactured by Kao Corporation) | 0.4 |
| N-(hexadesiloxyhydroxypropyl)-N-hydroxyethyl hexadecanamide (Sphingolipid E, manufactured by Kao Corporation) | 2.0 |
| Glycerin | 5.0 |
| Coloring agent | Trace amount |
| Fragrance | Trace amount |
| Purified water | Balance |
| Total | 100 |

Example 25 (Tint Emulsion)

A tint emulsion with the below-mentioned composition was produced in the same manner as that of Example 2. The number-average particle diameter of emulsion particles was 1.8 μm.

The produced emulsion could diminish skin color unevenness, could naturally cover the skin color unevenness, had no stickiness, and had excellent usability and good preservation stability.

| (Component) | |
|---|---|
| Olive oil (Cropure OL-LQ-(JP), manufactured by Croda Japan K. K.) | 8.0 (% by mass) |
| Neopentyl glycol dicaprate (Estemol N-01, manufactured by the Nisshin OiliO Group, Ltd.) | 2.0 |
| Microcrystalline wax (melting point: 65° C. to 85° C.) (Multiwax W-445, manufactured by Sonneborn, LLC) | 1.5 |
| Polyethylene wax (melting point: 95° C. to 105° C.) (PERFORMALENE 655, manufactured by NEW PHASE TECHNOLOGIES) | 1.5 |
| Stearyl alcohol | 1.0 |
| Cetanol | 1.5 |
| Distearyl dimethyl ammonium chloride (VARISOFT TA 100, manufactured by Evonik Industries AG) | 0.6 |
| Polyoxyethylene (20) hydrogenated castor oil (HLB: 10.5) (Nikkol HCO-20, manufactured by Nihon Surfactant Kogyo K. K.) | 1.4 |
| N-(hexadesiloxyhydroxypropyl)-N-hydroxyethyl hexadecanamide (Sphingolipid E, manufactured by Kao Corporation) | 2.0 |
| Glycerin | 5.0 |
| Coloring agent | Trace amount |
| Fragrance | Trace amount |
| Purified water | Balance |
| Total | 100 |

Example 26 (Oil-in-Water Emulsion Foundation)

An oil-in-water emulsion foundation with the below-mentioned composition was produced in the same manner as that of Example 2. The number-average particle diameter of emulsion particles was 1.5 μm.

The produced oil-in-water emulsion foundation could diminish skin color unevenness, could naturally cover the skin color unevenness, had no stickiness, and had excellent usability and good preservation stability.

| (Component) | |
|---|---|
| Olive oil (Cropure OL-LQ-(JP), manufactured by Croda Japan K. K.) | 8.0 (% by mass) |
| Neopentyl glycol dicaprate (Estemol N-01, manufactured by the Nisshin OiliO Group, Ltd.) | 2.0 |
| Ceresin (melting point: 72° C. to 76° C.) (Ceresin #810K, manufactured by Nikko Rica Corporation) | 2.5 |
| High-melting-point paraffin wax (melting point: 70° C. to 78° C.) (HNP-9, manufactured by Nippon Seiro Co., Ltd.) | 2.5 |
| Stearyl alcohol | 1.0 |
| Cetanol | 1.5 |
| N-stearoyl-L-glutamic acid (Amisoft HA-P; Ajinomoto Co., Inc.) | 0.6 |
| Polyoxyethylene (20) 2-hexyldecyl ether (HLB: 14) (Emulgen 1620G, manufactured by Kao Corporation) | 0.4 |
| L-arginine | 0.4 |
| Ceramide III (manufactured by Degussa) | 2.0 |
| Glycerin | 5.0 |

-continued

| (Component) | |
|---|---|
| Coloring agent | Trace amount |
| Fragrance | Trace amount |
| Purified water | Balance |
| Total | 100 |

Examples 27 to 48

Oil-in-water emulsion skin cosmetic compositions having each of the compositions shown in Table 3 to Table were produced using a 2-L beaker in the same manner as that of Example 2. The diameter of an emulsion particle was measured, and at the same time, the diminishment of skin color unevenness (covering power), no stickiness, preservation stability, smoothness and moist feeling were evaluated. The results are also shown in Table 3 and Table 5.

TABLE 3

| | Component (% by mass) | Example 27 | Example 28 | Example 29 | Example 30 |
|---|---|---|---|---|---|
| A | Olive oil (Cropure OL-LQ-(JP), manufactured by Croda Japan K. K.) | 6.7 | 6.7 | 6.7 | 6.7 |
| B | Ceresin (melting point: 72° C. to 76° C.) (Ceresin #810K, manufactured by Nikko Rica Corporation) | 1.5 | 1.5 | 1.5 | 1.5 |
| | High-melting-point paraffin (melting point: 70° C. to 78° C.) (HNP-9, manufactured by Nippon Seiro Co., Ltd.) | 1.5 | 1.5 | 1.5 | 1.5 |
| | Vaseline (melting point: 55° C. to 60° C.) (Super White Protopet, manufactured by Sonneborn, LLC) | | | | |
| C | Stearyl alcohol | 0.6 | 0.6 | 0.6 | 0.6 |
| | Cetanol | 0.9 | 0.9 | 0.9 | 0.9 |
| D | Distearyl dimethyl ammonium chloride (VARISOFT TA 100, manufactured by Evonik Industries AG) | 0.2 | 0.3 | 0.45 | 0.5 |
| | Polyoxyethylene (20) 2-hexyldecyl ether (HLB: 14) (Emulgen 1620G, manufactured by Kao Corporation) | 0.4 | 0.3 | 0.15 | 0.1 |
| F | Polyoxyethylene methyl glucoside (refractive index: 1.47) (MACBIOBRIDE MG-20E(MS), manufactured by NOF Corporation) | 1 | 1 | 1 | 1 |
| G | N-(hexadesiloxyhydroxypropyl)-N-hydroxyethyl hexadecanamide (Sphingolipid E, manufactured by Kao Corporation) | 2 | 2 | 2 | 2 |
| | Glycerin (refractive index: 1.45) | 10 | 10 | 10 | 10 |
| E | Purified water | 75.2 | 75.2 | 75.2 | 75.2 |
| | Total | 100 | 100 | 100 | 100 |
| | B/A | 0.45 | 0.45 | 0.45 | 0.45 |
| | Cationic surfactant/nonionic surfactant | 0.5 | 1.0 | 3.0 | 5.0 |
| | Number-average particle diameter (μm) | 2 | 2 | 2 | 2 |
| | Diminishment of skin color unevenness (covering power) (ΔY) | 3.5 | 3.5 | 3.5 | 3.5 |
| | No stickiness | 10 | 10 | 10 | 10 |
| | Preservation stability: | | | | |
| | room temperature, 1 month | b | b | b | b |
| | 50° C., 1 month | b | b | b | b |
| | Smoothness | 6 | 8 | 10 | 10 |
| | Moist feeling | 10 | 10 | 8 | 6 |

TABLE 4

| | Component (% by mass) | Example 31 | Example 32 | Example 33 | Example 34 | Example 35 | Example 36 | Example 37 |
|---|---|---|---|---|---|---|---|---|
| A | Olive oil (Cropure OL-LQ-(JP), manufactured by Croda Japan K. K.) | | | | 6.7 | 6.7 | 6.7 | 6.7 |
| | Isotridecyl isononanoate (Salacos 913, manufactured by the Nisshin OiliO Group, Ltd.) | 6.7 | | | | | | |
| | Squalane (Nikkol Squalane, manufactured by Nikko Chemicals Co., Ltd.) | | 6.7 | | | | | |
| | Dimethylpolysiloxane (Silicone KF-96A-6CS, manufactured by Shin-Etsu Chemical Co., Ltd.) | | | 6.7 | | | | |

TABLE 4-continued

| | Component (% by mass) | Example | | | | | | |
|---|---|---|---|---|---|---|---|---|
| | | 31 | 32 | 33 | 34 | 35 | 36 | 37 |
| B | Ceresin (melting point: 72° C. to 76° C.)<br>(Ceresin #810K, manufactured by Nikko Rica Corporation) | 1.5 | 1.5 | 1.5 | | | | |
| | High-melting-point paraffin (melting point: 70° C. to 78° C.)<br>(HNP-9, manufactured by Nippon Seiro Co., Ltd.) | 1.5 | 1.5 | 1.5 | 1.5 | | 1.5 | 1.5 |
| | Microcrystalline wax (melting point: 76° C. to 82° C.)<br>(Multiwax W-445 S, manufactured by Sonneborn, LLC) | | | | 1.5 | | | |
| | Polyethylene wax (melting point: 95° C. to 105° C.)<br>(PERFORMALENE 655, manufactured by NEW PHASE TECHNOLOGIES) | | | | | 1.5 | | |
| | Polyolefin wax (melting point: 85° C. to 105° C.)<br>(PERFORMALENE 700EP, manufactured by NEW PHASE TECHNOLOGIES) | | | | | | 1.5 | |
| | Beeswax (melting point: 62° C. to 67° C.)<br>(Golden Brand, manufactured by Miki Chemical Industry & Co., Ltd.) | | | | | | | 3.0 |
| C | Stearyl alcohol | 0.6 | 0.6 | 0.6 | 0.6 | 0.6 | 0.6 | 0.6 |
| | Cetanol | 0.9 | 0.9 | 0.9 | 0.9 | 0.9 | 0.9 | 0.9 |
| D | Distearyl dimethyl ammonium chloride<br>(VARISOFT TA 100, manufactured by Evonik Industries AG) | 0.4 | 0.4 | 0.4 | 0.4 | 0.4 | 0.4 | 0.4 |
| | Polyoxyethylene (20) 2-hexyldecyl ether (HLB: 14)<br>(Emulgen 1620G, manufactured by Kao Corporation) | 0.2 | 0.2 | 0.2 | 0.2 | 0.2 | 0.2 | 0.2 |
| F | Polyoxyethylene methyl glucoside (refractive index: 1.47)<br>(MACBIOBRIDE MG-20E(MS), manufactured by<br>NOF Corporation) | 1 | 1 | 1 | 1 | 1 | 1 | 1 |
| G | N-(hexadesiloxyhydroxypropyl)-N-hydroxyethyl hexadecanamide<br>(Sphingolipid E, manufactured by Kao Corporation) | 2 | 2 | 2 | 2 | 2 | 2 | 2 |
| | Glycerin (refractive index: 1.45) | 10 | 10 | 10 | 10 | 10 | 10 | 10 |
| E | Purified water | 75.2 | 75.2 | 75.2 | 75.2 | 75.2 | 75.2 | 75.2 |
| | Total | 100 | 100 | 100 | 100 | 100 | 100 | 100 |
| | B/A | 0.45 | 0.45 | 0.45 | 0.45 | 0.45 | 0.45 | 0.45 |
| | Cationic surfactant/nonionic surfactant | 2.0 | 2.0 | 2.0 | 2.0 | 2.0 | 2.0 | 2.0 |
| | Number-average particle diameter (μm) | 2 | 2 | 2 | 2 | 2 | 2 | 2 |
| | Diminishment of skin color unevenness (covering power) (ΔY) | 3.5 | 4.1 | 4.2 | 3.5 | 3.5 | 3.5 | 4.1 |
| | No stickiness | 10 | 10 | 10 | 10 | 10 | 10 | 9 |
| | Preservation stability: room temperature, 1 month | b | b | b | b | b | b | b |
| | 50° C., 1 month | b | b | b | b | b | b | b |
| | Smoothness | 10 | 10 | 10 | 10 | 10 | 10 | 10 |
| | Moist feeling | 10 | 10 | 10 | 10 | 10 | 10 | 10 |

TABLE 5

| | Component (% by mass) | Example | | | | | | | | | | |
|---|---|---|---|---|---|---|---|---|---|---|---|---|
| | | 38 | 39 | 40 | 41 | 42 | 43 | 44 | 45 | 46 | 47 | 48 |
| A | Olive oil<br>(Cropure OL-LQ-(JP), manufactured by Croda Japan K. K.) | 6.7 | 6.7 | 6.7 | 6.7 | 6.7 | 6.7 | 6.7 | 6.7 | 6.7 | 6.7 | 6.7 |
| B | Ceresin (melting point: 72° C. to 76° C.)<br>(Ceresin #810K, manufactured by Nikko Rica Corporation) | 1.5 | 1.5 | 1.5 | 1.5 | 1.5 | 1.5 | 1.5 | 1.5 | 1.5 | 1.5 | 1.5 |
| | High-melting-point paraffin (melting point: 70° C. to 78° C.)<br>(HNP-9, manufactured by Nippon Seiro Co., Ltd.) | 1.5 | 1.5 | 1.5 | 1.5 | 1.5 | 1.5 | 1.5 | 1.5 | 1.5 | 1.5 | 1.5 |
| C | Stearyl alcohol | 0.4 | 0.8 | 1.0 | 1.2 | 0.6 | 0.6 | 0.6 | 0.6 | 0.6 | 0.6 | 0.6 |
| | Cetanol | 0.6 | 1.2 | 1.5 | 1.8 | 0.9 | 0.9 | 0.9 | 0.9 | 0.9 | 0.9 | 0.9 |
| | Behenyl alcohol | | | | | 0.5 | | | | | | |
| D | Distearyl dimethyl ammonium chloride<br>(VARISOFT TA 100, manufactured by Evonik Industries AG) | 0.4 | 0.4 | 0.4 | 0.4 | 0.4 | 0.1 | 0.2 | 0.4 | 0.5 | | 0.4 |
| | Dicetyl dimethyl ammonium chloride<br>(VARISOFT 432 PPG, manufactured by Evonik Industries AG) | | | | | | | | | | 0.4 | |
| | Polyoxyethylene (20) 2-hexyldecyl ether (HLB: 14)<br>(Emulgen 1620G, manufactured by Kao Corporation) | 0.2 | 0.2 | 0.2 | 0.2 | 0.2 | 0.1 | 0.2 | 0.4 | 0.5 | 0.2 | |
| | Polyoxyethylene (40) hydrogenated castor oil (HLB: 12.5)<br>(Emanone CH-40, manufactured by Kao Corporation) | | | | | | | | | | | 0.2 |
| F | Polyoxyethylene methyl glucoside (refractive index: 1.47)<br>(MACBIOBRIDE MG-20E(MS), manufactured by NOF Corporation) | 1 | 1 | 1 | 1 | 1 | 1 | 1 | 1 | 1 | 1 | 1 |
| G | N-(hexadesiloxyhydroxypropyl)-N-hydroxyethyl hexadecanamide<br>(Sphingolipid E, manufactured by Kao Corporation) | 2 | 2 | 2 | 2 | 2 | 2 | 2 | 2 | 2 | 2 | 2 |
| | Glycerin (refractive index: 1.45) | 10 | 10 | 10 | 10 | 10 | 10 | 10 | 10 | 10 | 10 | 10 |
| E | Purified water | 75.7 | 74.7 | 74.2 | 73.7 | 74.7 | 75.6 | 75.4 | 75 | 74.8 | 75.2 | 75.2 |
| | Total | 100 | 100 | 100 | 100 | 100 | 100 | 100 | 100 | 100 | 100 | 100 |
| | B/A | 0.45 | 0.45 | 0.45 | 0.45 | 0.45 | 0.45 | 0.45 | 0.45 | 0.45 | 0.45 | 0.45 |
| | Cationic surfactant/nonionic surfactant | 2.0 | 2.0 | 2.0 | 2.0 | 2.0 | 1.0 | 1.0 | 1.0 | 1.0 | 2.0 | 2.0 |
| | Number-average particle diameter (μm) | 2 | 2 | 2 | 2 | 2 | 2 | 2 | 2 | 2 | 2 | 2 |

TABLE 5-continued

| Component (% by mass) | Example | | | | | | | | | | |
|---|---|---|---|---|---|---|---|---|---|---|---|
| | 38 | 39 | 40 | 41 | 42 | 43 | 44 | 45 | 46 | 47 | 48 |
| Diminishment of skin color unevenness (covering power) (ΔY) | 3.5 | 3.5 | 3.5 | 3.5 | 3.5 | 3.5 | 3.5 | 3.5 | 3.5 | 3.5 | 3.5 |
| No stickiness | 10 | 10 | 8 | 7 | 10 | 10 | 10 | 10 | 10 | 10 | 10 |
| Preservation stability: room temperature, 1 month | b | b | b | b | b | b | b | b | b | b | b |
| 50° C., 1 month | b | b | b | b | b | c | c | b | b | b | b |
| Smoothness | 10 | 10 | 10 | 10 | 10 | 8 | 8 | 7 | 6 | 10 | 10 |
| Moist feeling | 10 | 10 | 10 | 10 | 10 | 10 | 10 | 10 | 10 | 10 | 10 |

Examples 49 to 57 and Comparative Examples 12 to 15

1 kg of the makeup base of Example 4 was produced using a 2-L beaker by the below-mentioned steps. The diameter of an emulsion particle was measured, and at the same time, the diminishment of skin color unevenness (covering power), no stickiness, preservation stability, smoothness and moist feeling were evaluated. The results are shown in Table 6.

(Step 1) An oil phase comprising the components (A) to (D) and (G) and other oil agent components was heated to 80° C., and the oil phase was then stirred to obtain a mixture (1).

(Step 2) The components (E) and (F) and other water-soluble components were mixed with one another, and the obtained mixture was then heated to 80° C. Using a disperser, the thus heated mixture was mixed with the mixture (1) that had been heated to 80° C., whereby a mixture (2) was obtained. With regard to a stirring rate and a stirring time, the conditions shown in Table 6 were applied.

(Step 3) The mixture (2) was supplied to an oscillating-type stirring mixing device (VIBRO MIXER manufactured by REICA Co., Ltd.) by a proportioning pump. Thereafter, the mixture was continuously cooled to 30° C. at a rate of 30° C./min, while being stirred in the device, whereby an oil-in-water emulsion skin cosmetic composition was obtained.

(C) from 0.7 to 3.5% by mass of a linear alcohol having 12 to 22 carbon atoms, (D) from 0.2 to 1% by mass of a combination of a cationic surfactant and a nonionic surfactant having an HLB of 12.5 to 15, and (E) water, wherein the mass ratio of component (B) to component (A), (B)/(A), is from 0.3 to 1.0, emulsion particles have a number-average particle diameter of 1.0 to 3.0 μm, and the mass ratio of cationic surfactant to nonionic surfactant, cationic surfactant/nonionic surfactant, is from 1.5 to 5.0.

2. The oil-in-water emulsion skin cosmetic composition according to claim 1, wherein component (A) is an ester oil, and component (B) is a hydrocarbon oil.

3. The oil-in-water emulsion skin cosmetic composition according to claim 1, wherein component (B) is an oil agent having a melting point of 65 to 110° C.

4. The oil-in-water emulsion skin cosmetic composition according to claim 1, which further comprises:

(F) from 0.5% to 3% by mass of a water-soluble solvent having a refractive index of 1.46 to 1.55.

5. The oil-in-water emulsion skin cosmetic composition according to claim 1, which further comprises:

(G) from 1 to 3% by mass of a compound selected from the group consisting of ceramide and a ceramide analog.

TABLE 6

| Condition | Example | | | | | | | | | Comparative Example | | | |
|---|---|---|---|---|---|---|---|---|---|---|---|---|---|
| | 49 | 50 | 51 | 52 | 53 | 54 | 55 | 56 | 57 | 12 | 13 | 14 | 15 |
| Rate of disperser (rpm) | 8000 | 4500 | 3500 | 3500 | 2000 | 1400 | 3500 | 1400 | 1400 | 8000 | 8000 | 1400 | 1400 |
| Stirring time (min) | 3 | 15 | 3 | 0.5 | 3 | 10 | 0.25 | 3 | 1 | 60 | 15 | 0.4 | 0.2 |
| Input energy [kJ/m³] | 8700 | 7800 | 730 | 125 | 136 | 155 | 61 | 47 | 15 | 174760 | 43700 | 6 | 3 |
| Number-average particle diameter (μm) | 1.0 | 1.0 | 1.5 | 2.0 | 2.0 | 2.0 | 2.5 | 2.5 | 3.0 | 0.5 | 0.75 | 3.5 | 4.0 |
| Diminishment of skin color unevenness (covering power) (ΔY) | 3.9 | 39 | 3.8 | 3.5 | 3.5 | 3.5 | 3.8 | 3.8 | 3.9 | 4.5 | 4.5 | 4.5 | 4.5 |
| No stickiness | 10 | 10 | 10 | 10 | 10 | 10 | 9 | 9 | 9 | 10 | 10 | 8 | 8 |
| Preservation stability: room temperature, 1 month | b | b | b | b | b | b | b | b | b | b | b | b | b |
| 50° C., 1 month | b | b | b | b | b | b | b | b | b | b | b | b | b |
| smoothness | 10 | 10 | 10 | 10 | 10 | 10 | 10 | 10 | 10 | 9 | 10 | 7 | 6 |
| Moist feeling | 10 | 10 | 10 | 10 | 10 | 10 | 10 | 10 | 10 | 7 | 7 | 9 | 10 |

The invention claimed is:

1. An oil-in-water emulsion skin cosmetic composition comprising components (A), (B), (C), (D) and (E):

(A) from 1 to 10% by mass of an oil agent which is liquid at 25° C., (B) from 1 to 6% by mass of an oil agent which is solid or semi-solid at 25° C.,

6. The oil-in-water emulsion skin cosmetic composition according to claim 1, wherein the cationic surfactant is at least one member selected from the group consisting of dicetyl dimethyl ammonium chloride and distearyl dimethyl ammonium chloride.

7. The oil-in-water emulsion skin cosmetic composition according to claim 1, wherein the nonionic surfactant is at least one member selected from the group consisting of polyoxyethylene alkyl ether and polyoxyethylene hydrogenated castor oil.

8. A method for adjusting the appearance of skin, which comprises applying the oil-in-water emulsion skin cosmetic composition according to claim 1 to the skin.

9. The oil-in-water emulsion skin cosmetic composition according to claim 1, wherein the mass ratio of cationic surfactant to nonionic surfactant, cationic surfactant/nonionic surfactant, is from 1.5 to 3.0.

10. The oil-in-water emulsion skin cosmetic composition according to claim 1, wherein the mass ratio of cationic surfactant to nonionic surfactant, cationic surfactant/nonionic surfactant, is from 1.5 to 2.5.

* * * * *